(12) United States Patent
Selmon et al.

(10) Patent No.: US 6,398,798 B2
(45) Date of Patent: *Jun. 4, 2002

(54) CATHETER SYSTEM FOR TREATING A VASCULAR OCCLUSION

(75) Inventors: Matthew R. Selmon, Woodside; Gerald Hansen, Newark; Charles Milo, Union City, all of CA (US)

(73) Assignee: LuMend, Inc., Redwood City, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 11 days.

This patent is subject to a terminal disclaimer.

(21) Appl. No.: 09/032,773

(22) Filed: Feb. 28, 1998

(51) Int. Cl.[7] .............................. A61B 17/22; A61D 1/02

(52) U.S. Cl. ...................................................... 606/159

(58) Field of Search .................. 606/159, 170, 606/171, 167, 205

(56) References Cited

U.S. PATENT DOCUMENTS

| | | | |
|---|---|---|---|
| 832,201 A | 10/1906 | Kistler | |
| 1,127,948 A | 2/1915 | Wappler | |
| 1,267,066 A | 5/1918 | Flack | |
| 2,621,651 A | 12/1952 | Wallace | 128/4 |
| 3,640,270 A | 2/1972 | Hoffmann | 128/2.1 E |
| 3,667,474 A | 6/1972 | Lapkin et al. | 128/345 |
| 4,043,323 A | 8/1977 | Komiya | 128/4 |
| 4,355,643 A | 10/1982 | Laughlin et al. | 128/663 |
| 4,541,433 A | 9/1985 | Baudino | 128/668 |
| 4,572,186 A | 2/1986 | Gould et al. | 128/341 |
| 4,585,000 A | 4/1986 | Hershenson | 128/345 |
| RE32,158 E | 5/1986 | Vukovic | 128/6 |
| 4,630,609 A | 12/1986 | Chin | 128/334 |
| 4,648,402 A | 3/1987 | Santos | 128/345 |
| 4,669,467 A | 6/1987 | Willett et al. | 128/303.1 |
| 4,681,110 A | 7/1987 | Wiktor | 128/343 |
| 4,698,057 A | 10/1987 | Joishy | 604/176 |
| 4,723,549 A | 2/1988 | Wholey et al. | 128/344 |
| 4,737,142 A | 4/1988 | Heckele | 604/95 |

(List continued on next page.)

FOREIGN PATENT DOCUMENTS

| | | | |
|---|---|---|---|
| DE | 2945237 A1 | 5/1981 | A61B/17/22 |
| DE | 4429117 A1 | 2/1996 | A61M/29/00 |
| EP | 0 377 269 A1 | 7/1990 | A61M/25/01 |
| EP | 0 521 595 A2 | 1/1993 | A61M/25/01 |
| EP | 0643980 A1 | 3/1995 | A61M/29/00 |
| FR | 1585065 | 1/1970 | |
| RU | 134398 | 1/1960 | |
| WO | WO83/03188 | 9/1983 | A61B/1/06 |
| WO | WO 91/02493 | 3/1991 | A61B/17/22 |
| WO | WO91/19528 | 12/1991 | A61M/29/00 |
| WO | WO92/08510 | 5/1992 | A61M/25/00 |
| WO | WO93/18818 | 9/1993 | A61M/37/00 |
| WO | WO95/19143 | 7/1995 | A61B/17/22 |
| WO | WO96/01590 | 1/1996 | A61B/17/22 |
| WO | WO96/11636 | 4/1996 | A61B/17/28 |
| WO | WO 99/40963 | 8/1999 | A61M/29/00 |

Primary Examiner—Michael Buiz
Assistant Examiner—Vy Q. Bui
(74) Attorney, Agent, or Firm—Perkins Coie LLP

(57) ABSTRACT

A catheter system and method are provided including a blunt end assembly with a catheter and a blunt end member. The blunt end member includes jaw sections which have a first position or closed position for locating the blunt end member at the site of the occlusion within the native lumen of the blood vessel and a second position or open position wherein the jaw sections are able to press against the interior walls of the lumen adjacent the occlusion. The assembly includes an actuation member for moving the jaw sections from the closed to the open positions repeatedly resulting in a fracturing of the occlusion. A guide wire may be thread through an internal opening in the catheter and the blunt end member and after fracturing, across the occlusion.

24 Claims, 3 Drawing Sheets

U.S. PATENT DOCUMENTS

| | | | | |
|---|---|---|---|---|
| 4,787,388 | A | 11/1988 | Hofmann | 128/344 |
| 4,794,928 | A | 1/1989 | Kletschka | 128/344 |
| 4,848,336 | A | 7/1989 | Fox et al. | 128/303.1 |
| 4,862,874 | A | 9/1989 | Kellner | 128/6 |
| 4,919,112 | A | 4/1990 | Siegmund | 128/4 |
| 5,001,556 | A | 3/1991 | Nakamura et al. | 358/98 |
| 5,011,488 | A | 4/1991 | Ginsburg | 606/159 |
| 5,019,040 | A | 5/1991 | Itaoka et al. | 604/95 |
| 5,030,201 | A | 7/1991 | Palestrant | 604/22 |
| 5,034,001 | A | 7/1991 | Garrison et al. | 604/53 |
| 5,089,006 | A | 2/1992 | Stiles | 606/198 |
| 5,092,839 | A | 3/1992 | Kipperman | 604/53 |
| 5,098,381 | A | 3/1992 | Schneider | 604/96 |
| 5,099,850 | A | 3/1992 | Matsui et al. | 128/662.06 |
| 5,100,425 | A | 3/1992 | Fischell et al. | 606/159 |
| 5,102,390 | A | 4/1992 | Crittenden et al. | 604/96 |
| 5,114,414 | A | 5/1992 | Buchbinder | 604/95 |
| 5,156,594 | A | 10/1992 | Keith | 604/96 |
| 5,179,961 | A | 1/1993 | Littleford et al. | 128/772 |
| 5,180,368 | A | 1/1993 | Garrison | 604/104 |
| 5,192,290 | A | 3/1993 | Hilal | 606/159 |
| 5,193,546 | A | 3/1993 | Shaknovich | 128/662.06 |
| 5,197,971 | A | 3/1993 | Bonutti | 606/192 |
| 5,209,729 | A | 5/1993 | Hofmann et al. | 604/96 |
| 5,211,654 | A | 5/1993 | Kaltenbach | 606/191 |
| 5,217,484 | A | 6/1993 | Marks | 606/200 |
| 5,263,959 | A | 11/1993 | Fischell | 606/180 |
| 5,263,963 | A | 11/1993 | Garrison et al. | 606/198 |
| 5,279,565 | A * | 1/1994 | Klein et al. | 604/105 |
| 5,282,817 | A | 2/1994 | Hoogeboom et al. | 606/167 |
| 5,304,199 | A | 4/1994 | Myers | 606/194 |
| 5,321,501 | A | 6/1994 | Swanson et al. | 356/345 |
| 5,334,210 | A | 8/1994 | Gianturco | 606/151 |
| 5,336,252 | A | 8/1994 | Cohen | 607/119 |
| 5,350,377 | A | 9/1994 | Winston et al. | 606/15 |
| 5,351,678 | A | 10/1994 | Clayton et al. | 128/6 |
| 5,383,467 | A | 1/1995 | Auer et al. | 128/664 |
| 5,409,453 | A | 4/1995 | Lundquist et al. | 604/22 |
| 5,415,636 | A | 5/1995 | Forman | 604/101 |
| 5,423,846 | A | 6/1995 | Fischell | 606/180 |
| 5,439,000 | A | 8/1995 | Gunderson et al. | 128/664 |
| 5,456,667 | A | 10/1995 | Ham et al. | 604/107 |
| 5,459,570 | A | 10/1995 | Swanson et al. | 356/345 |
| 5,484,412 | A | 1/1996 | Pierpont | 604/101 |
| 5,486,170 | A | 1/1996 | Winston et al. | 606/16 |
| 5,486,193 | A | 1/1996 | Bourne et al. | 606/194 |
| 5,490,859 | A | 2/1996 | Mische et al. | 606/159 |
| 5,499,995 | A | 3/1996 | Teirstein | 606/192 |
| 5,501,694 | A | 3/1996 | Ressemann et al. | 606/159 |
| 5,507,295 | A | 4/1996 | Skidmore | 128/662.06 |
| 5,507,296 | A | 4/1996 | Bales et al. | 128/751 |
| 5,511,559 | A | 4/1996 | Vance | 128/772 |
| 5,522,819 | A | 6/1996 | Graves et al. | 606/113 |
| 5,540,707 | A | 7/1996 | Ressemann et al. | 606/159 |
| 5,556,408 | A | 9/1996 | Farhat | 606/180 |
| 5,573,531 | A | 11/1996 | Gregory | 606/14 |
| 5,599,306 | A | 2/1997 | Klein et al. | 604/96 |
| 5,618,300 | A | 4/1997 | Marin et al. | 606/198 |
| 5,626,599 | A | 5/1997 | Bourne et al. | 606/194 |
| 5,626,607 | A | 5/1997 | Malecki et al. | 606/205 |
| 5,653,684 | A | 8/1997 | Laptewicz et al. | 604/22 |
| 5,688,234 | A | 11/1997 | Frisbie | 604/22 |
| 5,707,390 | A | 1/1998 | Bonutti | 606/204 |
| 5,713,907 | A | 2/1998 | Hogendijk et al. | 606/108 |
| 5,766,151 | A | 6/1998 | Valley et al. | 604/96 |
| 5,800,450 | A | 9/1998 | Lary et al. | 606/180 |
| 5,816,923 | A | 10/1998 | Milo et al. | 464/58 |
| 6,010,449 | A * | 1/2000 | Selmon et al. | 600/117 |
| 6,015,423 | A | 1/2000 | Andrese | 606/198 |

* cited by examiner

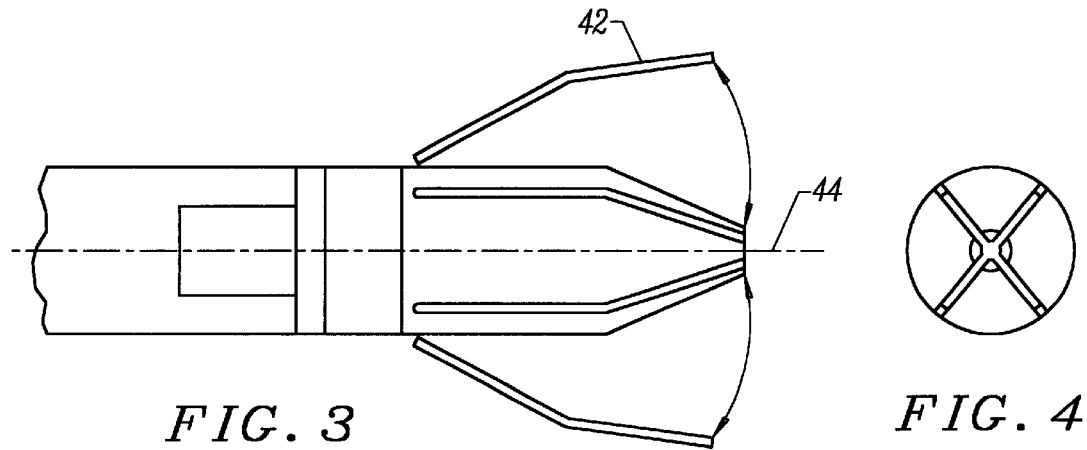
*FIG. 3*
*FIG. 4*
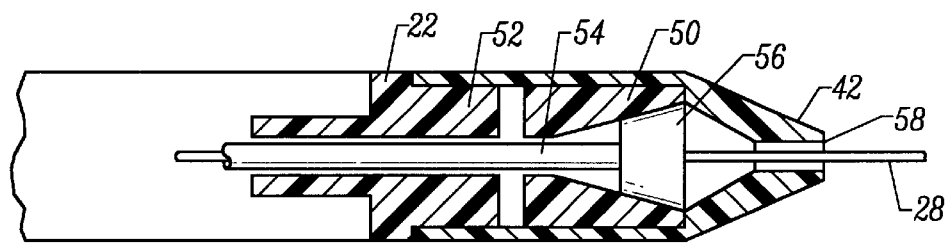
*FIG. 5*
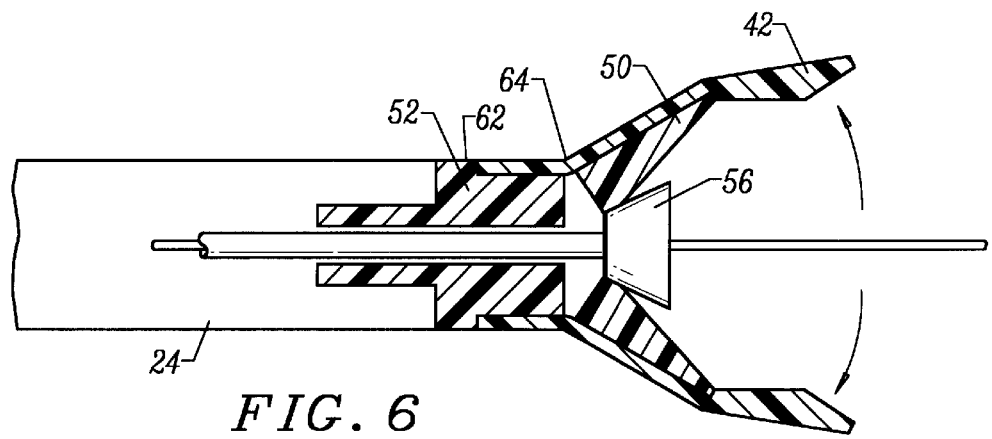
*FIG. 6*

CATHETER SYSTEM FOR TREATING A VASCULAR OCCLUSION

This application is related to and claims the benefit of U.S. Provisional application No. 60/050,913 filed Feb. 28, 1997; and U.S. Pat. application No. 08/775,264 filed Feb. 28, 1997, now U.S. Pat. No. 5,968,064.

BACKGROUND OF THE INVENTION

1. Field of the Invention

This invention relates generally to medical devices. More particularly, this invention relates to intravascular catheters having the ability to fracture an occlusion sufficiently for allowing a guide wire to pass through the occlusion within the natural lumen of the blood vessel.

2. Background

Medical science has long sought effective treatments for disease conditions involving stenosis (narrowing obstruction) of the lumen (interior passage of the artery) of an artery. This condition, known generally as an occlusion, is found in patients suffering from atherosclerosis (accumulation of fibrous, fatty or calcified tissue in the arteries). An occlusion can manifest itself in hypertension (high blood pressure), ischemia (deficiency of circulation), angina (chest pain), myocardial infarction (heart attack), stroke, or death. An occlusion may be partial or total, may be soft and pliable or hard and calcified, and may be found at a great variety of sites in the arterial system including the aorta, the coronary and carotid arteries, and peripheral arteries.

Of particular interest to cardiac medicine are the often disabling or fatal occlusions occurring in the coronary arteries (arteries supplying the heart). Traditionally, coronary artery occlusions have been treated by performing coronary bypass surgery, in which a segment of the patient's saphenous vein is taken from the patient's leg and is grafted onto the affected artery at points proximal (upstream) and distal (downstream) to the occluded segment. The bypass often provides dramatic relief. However, it entails dangerous open chest surgery and a long, painful, costly convalescence in the hospital. Moreover, with the passage of time, the bypass patient's saphenous vein graft can also become occluded. If the patient has another saphenous vein, a second bypass procedure may be performed, once again entailing open chest surgery and prolonged hospitalization. Thereafter, if the underlying atherosclerotic disease process is not controlled, the prognosis is dismal.

Newer, minimally invasive procedures are now preferred in the treatment of arterial occlusions. These procedures use a catheter, a long, thin, highly flexible device which is introduced into a major artery through a small arterial puncture made in the groin, upper arm, or neck and is advanced and steered into the site of the stenosis. At the distal end of the catheter, a great variety of miniature devices have been developed for operating upon the stenosed artery.

The more popular minimally invasive procedures include percutaneous transluminal coronary angiopiasty (PTCA), directional coronary atherectomy (DCA), and stenting. PTCA employs a balloon to mechanically dilate the stenosis. In PTCA, a steerable guidewire is introduced and advanced under fluoroscopic observation into the stenosed artery and past the stenosis. Next, a balloon-tipped catheter is advanced over the guidewire until it is positioned across the stenosed segment. The balloon is then inflated, separating or fracturing the atheroma (stenosed tissue). The hoped-for outcome is that, over time, the lumen will stay open.

In directional coronary atherectomy, a catheter containing a cutter housed in its distal end is advanced over the guidewire into the stenosed segment. The housing is urged against the atheroma by the inflation of a balloon, so that part of the atheroma intrudes through a window in the side of the housing. Under fluoroscopic observation, the cutter is used to shave away the atheroma. The shavings are collected in the nosecone of the housing and withdrawn along with the catheter.

Stenting is a procedure in which a wire framework, known as a stent, is compressed and delivered using a balloon catheter. The stent is positioned across the stenosed segment of the artery. The balloon is inflated, dilating the stent and forcing the stent against the artery wall. The hoped-for outcome is that the stent will hold the arterial lumen open for a prolonged period. Frequently, a stent is placed in an artery immediately following PTCA or DCA.

It must be noted, however, that the aforementioned catheters are "over-the-wire catheters." These catheters depend on the guidewire, which typically has a tiny bent portion at its distal end for steering. Over-the-wire catheters cannot be positioned adjacent the stenosis until the guidewire has been advanced across the stenosed arterial segment. Thus, where the occlusion is too severe to be crossed by a guidewire or where there is not enough room for the balloon, cutter, or stent delivery catheter, neither PTCA nor DCA nor stenting can be done. Unfortunately, the occlusion often contains extremely hard, calcified tissue and presents an impenetrable barrier to the guidewire. Even a less than total occlusion may contain complex structures which divert or trap the steering end of the guidewire. Thus, the guidewire might not completely cross the occlusion, but become diverted into the subintimal space between the intima and the atheroma or become buried in the atheroma. In either case, the guidewire cannot be positioned across the stenosis to guide a balloon or cutting element. In such cases, bypass surgery may be necessary with the associated cost, risks, and recovery period.

Thus, in patients suffering from severe or total arterial occlusion, it is preferable to do what has been difficult or impossible in the past: to open the severely or totally occluded artery itself, rather than by performing a bypass. If a guidewire and working catheter can be passed through or around the atheroma, the severe or total occlusion can be treated by PTCA, DCA, stenting, site-specific drug delivery or a combination of these proven therapies.

It would be advantageous to find and open a path of low resistance, either through or around the atheroma. Of course, this must be done without perforating the arterial wall. Clearly, the serious consequences of penetrating the arterial wall must be avoided at all cost. The physician will not use a system which would be unsafe and no patient would want a physician to use such a system. Therefore, any solution to the problem of finding and creating an opening through or around the atheroma must be safe and in many instances include a system of guidance for the device that would find and open such an occlusion.

There has been a long felt need to provide a reliable system of guidance for such a device. As understood by those in the art, the device must travel a criss-crossing, often maze-like structure before it even gets to the occlusion. Then the occlusion itself is often a maze-like structure. Attempting to cross such an occlusion without reliable guidance is dangerous. For example, it is easy to dissect the tissues of the arterial wall instead of the occlusion, thereby creating a false lumen and possibly perforating the artery. If blood escapes the artery and accumulates in the pericardial space, it will compress the heart, requiring emergency intervention to avert heart failure and death.

One guidance system which has been used in conjunction with coronary catheterization is biplane fluoroscopy, wherein the interventionist observes two flat real-time x-ray images acquired from different angles. Biplane fluoroscopy, however, is unreliable, costly, and slow. Delay is unacceptable, for it contributes to trauma and stress and creates opportunities for complications and failures of technique.

Recently, promising optical systems have been disclosed for imaging an occlusion through a catheter placed in the artery. One such system is Optical Coherence Tomography (OCT). In OCT, a beam of light carried by an optical fiber illuminates the artery interior. In a radar-like manner, light reflected back into the fiber from features inside the artery is correlated with the emitted light to capture the depth as well as the angular separation of those features. The features are displayed graphically in two or three dimensions through the use of a suitably programmed computer.

The beam in OCT is swept by mechanical rotation or movement of optical components in the catheter, or by optical switching devices which select one of several fibers through which to perform measurements. The rotation is encoded, or the switching pattern recorded, for reconstructing angular information about the artery interior. For example, a beam splitter may be placed between the light source and the catheter fiber to produce a reference beam which is directed to a reflector at a known distance. The catheter beam and the reference beam are recombined as they return. When the paths traveled by the two beams are of equal optical length, interference fringes are observable in the combined beam. Since the lengths of the reference path and the catheter fiber are known, the distance from the fiber end to a particular reflective feature within the artery can be inferred. In OCT and related methods, signals many also be impressed upon the light beam to facilitate the measurement of distance or the detection of motion of objects relative to the fiber end. By means of OCT or other similar optical methods, imaging capability can be incorporated into an intravascular catheter or guidewire.

However, while superior imagery alone is of diagnostic interest, effective intervention for severe occlusive arterial disease is what is truly desired. Even with improved guidance, there persists a long felt need for working elements which are capable of opening a path through or around an arterial occlusion at low risk of perforating the artery. What is needed is an intravascular catheter system for the effective treatment of the severely occluded artery and, in particular, the totally occluded artery. What is especially needed is a therapeutic working element which allows the physician to mechanically fracture an occlusion or to separate the occlusion from the intimal surface, but which is operable in a manner unlikely to perforate the adventitia.

SUMMARY OF THE INVENTION

A method and apparatus are provided for bypassing a vascular occlusion. An intravascular catherer is positioned adjacent to the vascular occlusion. The intravascular catherer includes at least one distally mounted hinged section coupled to an actuation member. The hinged section is rotatably coupled among at least one open position and at least one closed position. The actuation member includes an actuation shaft coupled to control movement of the hinged section. The hinged section is opened to an open position in response to a force applied to the actuation member, and the vascular occlusion is displaced.

BRIEF DESCRIPTION OF THE DRAWINGS

For a further understanding of the objects and advantages of the present invention, reference should be had to the following detailed description, taken in conjunction with the accompanying drawings, in which like parts are given like reference numerals and wherein:

FIG. 3 is an enlarged side view of the blunt end member having a first closed position and a second open position.

FIG. 4 is an end view of the blunt end member of FIG. 3 in the first or closed position.

FIG. 5 is a cross sectional plane view of the blunt end member of FIG. 1 shown in cross sectional view.

FIG. 6 is a cross sectional view of the blunt end member of FIG. 1 shown in the second open position.

DETAILED DESCRIPTION OF THE INVENTION

Figure 1:
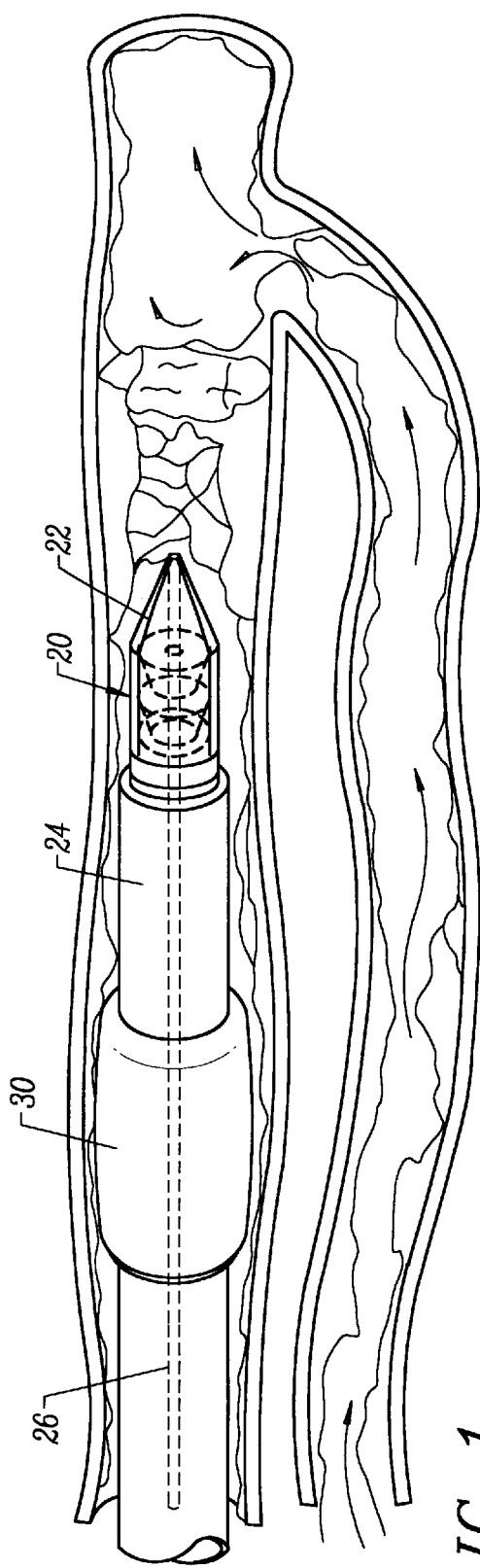
FIG. 1 illustrates an exemplary embodiment of the blunt end member for fracturing a total occlusion in accordance with this invention shown in partial cross section.
Figure 2:
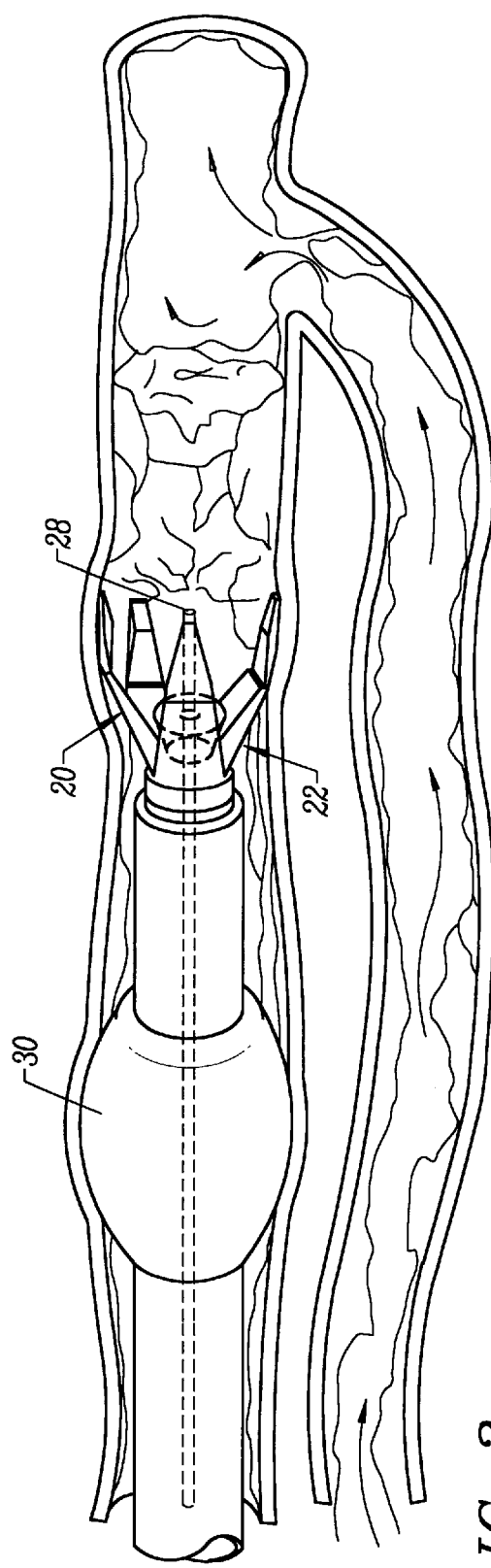
FIG. 2 is a partial cross sectional view of the catheter having the blunt end member of FIG. 1 in the process of fracturing the total occlusion.
Figure 7:
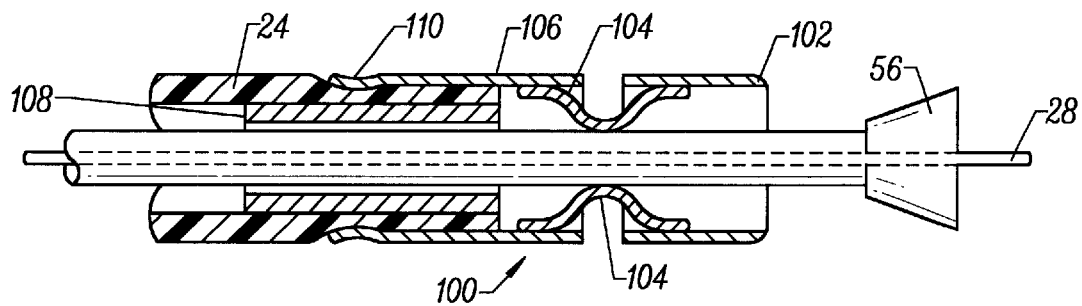
FIG. 7 is a cross sectional plane view of another exemplary embodiment of the blunt end member in accordance with this invention.
Figure 8:
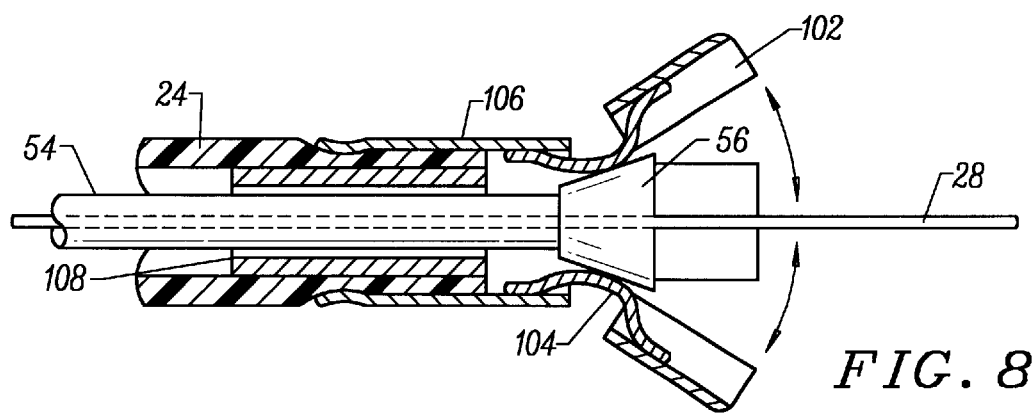
FIG. 8 is a cross sectional view of the blunt end member of FIG. 7 shown in the second open position.
Figure 9:
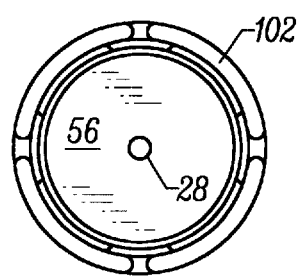
FIG. 9 is an end view of the blunt end member of FIG. 8.
Figure 10:
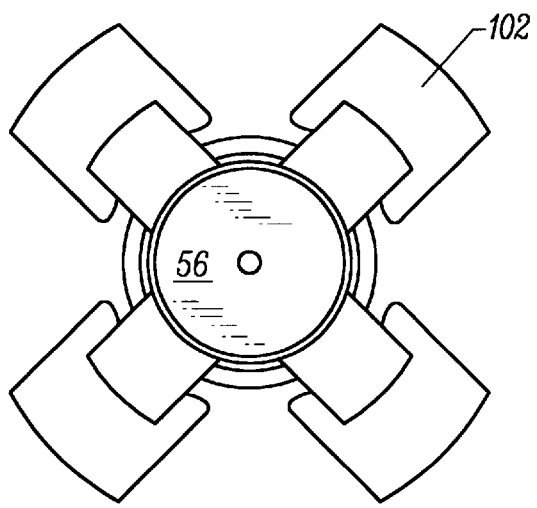
FIG. 10 is an enlarged end view of the blunt end member of FIG. 7 shown in the second or open position.

The invention is described particulary with reference to a coronary bypass arterial condition. As illustrated in FIGS. 1 and 2, the blunt end member, in accordance with this invention, is shown adjacent to a total occlusion where a bypass is in the process of failing. The bypass has developed diffuse stenosis as shown in FIGS. 1 and 2. It is likely that where stenosis has developed sufficiently to block an anterial blood vessel, stenosis will also accumulate following a bypass. Even, to the point that the bypass may also be blocked or become totally occluded. Using the blunt end member, in accordance with this invention, the original, native blood vessel is reopened allowing the bypass to fade as the primary source of blood flow.

It will of course be appreciated that the drawings are illustrative only, and that the invention may be used in any situation where the blood vessel, such as a coronary artery has been occluded, by stenosis or other arterial disease. The principal feature of the invention is to fracture the stenosis occluding blood flow and allow the native artery to resume the primary responsibility for blood flow.

With particular reference to FIG. 1, there is shown the blunt end member assembly in accordance with this invention, generally designated by the numeral 20. The assembly 20 includes a blunt end member, 22 and a catheter 24. An actuation member indicated by doted lines 26 moves the blunt end member from a first closed position as illustrated in FIG. 1 to an second open position as illustrated in FIG. 2.

The catheter is positioned using a guide wire 28 as best shown in FIG. 2, so that the extreme distal end of the blunt end member is adjacent to the total occlusion, as shown in FIGS. 1 and 2. Once positioned, the catherer of an embodiment can be stabilized using a stabilizing member for example, a balloon member 30. The balloon member 30 is inflated as shown in FIG. 2, so that the catheter remains in place during actuation of the blunt end member 22.

With particular reference to FIGS. 3 through 6, there is shown an exemplary first embodiment of the blunt end member 22. The blunt end member 22 has a proximal end 40 attached to the distal end of the catheter 24. The method of attachment is conventional within the skill and knowledge of the prior art.

The blunt end member includes a set of sectional members defining jaw sections 42. The jaw sections 42 are located at the distal end of the blunt end member and are spaced equal distance of the longitudinal center line 44. Thus, the jaw sections 42 open to a second position shown particularly in FIGS. 3 and 6, and close to a first position as shown in FIGS. 3, 4, and 5. An actuation member moves the jaw sections 42 from a first closed position to a second open position.

The jaw sections 42 are generally spade shaped and are separate from one another. This allows the jaw sections to meet flush against the arterial wall and the occlusion for optimizing fracturing of the occlusion. The jaw sections 42 are spaced as shown in FIG. 4.

With respect to FIGS. 5 and 6, there is shown an assembly view of the blunt end member 22 in accordance with the invention as illustrated in FIG. 4. FIG. 5 is a cross sectional view along line 5—5 of FIG. 4 and looking in the direction of the arrows. The blunt end member 22 includes a reverse conical urging member 50 and a spaced apart support member 52. The members 50 and 52 are sized and shaped to fit within the same cavity or lumen of the catheter 24.

Each of the members 50 and 52 includes a center opening along the longitudinal center line 44. The openings 50 and 52 are aligned so that a guide wire tube 54 can slide toward and away from the proximal end of the catheter 24.

Attached to the guide wire tube 14 is a ferrule 50. The ferrule 56 also has a center opening aligned with the center openings of the members of 50 and 52. However, the center opening of the ferrule 56 has a smaller diameter to match the guide wire 28 and not the guide wire tube 54. Thus, the ferrule 56 is designed to accommodate only the guide wire 28 and not the guide wire tube 4.

The guide wire 28 is shown inserted in the center opening of the ferrule 56. It will also be appreciated that the jaw sections 42 are spaced apart sufficient distance along the longitudinal center line 44 so that the guide wire is guided thereby. Therefore, the jaw sections 42, when closed, form a internal guide 58 for sliding the guide wire toward and away from the distal end of the catheter 24.

The ferrule 56 may be made from a variety of materials including stainless steel, nickel titanium or other shape memory alloys and various engineering plastics. Additionally, other polymers or metal materials, which are bio-compatible and have the mechanical characteristics necessary to perform the functions herein are equally suitable.

The ferrule defines a frusto-conical shape, while the urging member 50 forms a reverse compatible shape for sliding against the frusto conical shape of the ferrule 56. The surfaces where each of the ferrule 56 and the urging member 50 contact, define a mating surface. The materials selected for each of the ferrule 56 and urging member 50 are compatible for such mating sliding contact.

In response to actuation, the ferrule 56 is pulled toward the proximal end of the catheter 24 causing the ferrule 56 to slide against the urging member 50, the mating surfaces of each sliding across one another. As the ferrule is pulled towards the proximal end of the catheter, an increasing force is urged against the jaw sections 42 for spreading apart said jaw sections 42. Upon full activation of the actuation member the jaws are fully open.

In an embodiment of the invention, the blunt end jaw members 42 are made of material having sufficient strength to withstand the mechanical forces necessary to fracture the occlusion. In a preferred embodiment, the jaw sections are made from nickel titanium which has proven bio-compatible as well as having sufficient strength.

The guide wire tube 54 is bonded to the ferrule. The bonding may be similar to the bonding of the catheter and the blunt end member 22. Additionally, bonding may be done using adhesives such as loc-tite™, soldering, or chemical or physical bonding, of a suitable kind. As such, the guide wire tube 54 is permanently connected to the ferrule with a bond that is strong enough to withstand the urging forces exerted against the occlusion. The interior opening of the members 50 and 52, provides a guide for the guide wire tube 54 as the jaw sections 42 are opened and closed in repeated use. It may be advantages to coat the interior opening of the members 50 and 52 as well as the exterior of the guide wire 54, with Teflon or similar polymers so that any friction from sliding is greatly reduced. A reduction in friction will, of course, result in more force being applied by the ferrule 56 against the urging member 50 to maximize the amount of fracturing power generated by the blunt end member 42.

Conventionally, the guide wire tube 54 is a braided strand, and thus can be quite abrasive to the internal opening of the members of 50 and 52. Thus, the matter of applying a coating may be increasingly important to reduce the friction in sliding. Additionally, it is preferable that the mating surfaces of the urging member 50 and the ferrule 56 also be as smooth as possible and chosen from compatible materials to minimize the amount of friction developed as the mating surfaces slide against one another in an effort to fracture the occlusion. In an embodiment the ferrule and urging members are both made from nickel titanium. In another embodiment, the urging member 50 is made from stainless steel and the ferrule 56 is made from nickel titanium. Again, the mating surfaces of the ferrule 56 and urging member 50 are made as smooth as possible to minimize the friction there between.

The support member 52 provides support both internal and external to the assembly 20. The support member 52 remains fixedly attached to the distal end of the catheter 24 and provides an internal opening for the sliding movement of the guide wire tube 54. Additionally, the jaw sections 42 have a proximal end zone 60 which surrounds both the urging member 50 and the support member 52. The proximal end zone of the jaw sections 42 secures the members 50 and 52 together to provide the assembly 20. The support member is notched at shoulder 62 to provide a secure connection fit with the jaw sections 42.

The entire assembly, including members 50 and 52, as well as jaw sections 42, may be made from a single piece of nickel titanium (NiTi) for a unified assembly. In another embodiment the jaw sections are notched with an opening at elbow 64. This allows space for deformation of the jaw sections along an axis predetermined by the angle and length of the opening.

FIGS. 7 through 10 show another embodiment of the blunt end member 100. The blunt end member 100 includes jaw sections 102. The blunt end member 100 includes a spring member 104 and a support member 106. A reinforcing member 108 is positioned between the catheter tube 24 and the guide wire tube 54 in the guide wire lumen of the catheter tube 24. Attached to the guide wire tube 54 is a ferrule 56.

Similar to the reverse conical urging member 50, the spring member 104 has a mating surface for mating with the ferrule 56. Upon actuation, the ferrule 56 is pulled toward the proximal end of the catheter 24 and the mating surfaces engage and separate the jaw sections 102. Upon releasing the actuation member, the spring member 104 urges the jaw sections 102, back to their original and first closed positioned. The spring member 104 serves to connect the jaw sections 102 and the rest of the blunt end member 100, and specifically the support member 106. The support member 106 is crimped at its proximal end 110. The reinforcing member 108 is positioned so that the crimp in the support member 106 sandwiches the distal end of the catheter tube 24. The strength provided by the reinforcing member 108 enables a secure attachment of the support member to the distal end of the catheter tube 24. The crimp in the support member, plus the added hoop strength provided by the reinforcing member 108, provide a secure connection for the entire blunt end member 100.

The blunt end member is supported by the connections at the joining of the spring 104, the jaw sections 102, and support member 106. These connections can be made in a variety of ways. For example, it is preferable to bond the members with an epoxy, should they be made of a polymer or to use welding, soldering, or brazing, if the members are made from metal.

In an embodiment, the spring 104 is made from nickel titanium as are the support member 106 and jaw sections 102. In other embodiments, the support and spring members 106 and 104 are made using stainless steel. Additionally, the reinforcing member 108 may be made from nickel titanium or stainless steel. It is also contemplated that various other types of materials are suitable for manufacturing of the blunt end member 100.

In operation the blunt end member 100 is placed in a first closed position. As is typical in DCA operations, the guide wire 28 is fed through the lumen of the blood vessels of a patent and advanced to the occlusion. The blunt end member 100 with ferrule 56 is positioned directly adjacent to the occlusion. Although not shown, the balloon 30 may also be adapted for use with this embodiment.

After stabilization of the catheter 24 in the lumen of the blood vessel, the blunt end member 100 is activated by pulling on an actuation member such that the mating surfaces of the spring 104 and the ferrule 56 are brought into contact with one another. The ferrule 56 moves the jaw sections 102 away from the longitudinal center line 44 of the catheter as described earlier with reference to FIGS. 1 through 6. This operation is repeated until fracturing occurs, as clearly shown in FIG. 2. Once fracturing occurs, and the guide wire 28 can be fed through the natural lumen of the blood vessel, the catheter may be removed and another working end may be brought to bear upon the occlusion. Such working end may include an angioplasty device, atherectomy catheter device, or a stent or other known medical methods, for removing the occlusion once the guide wire 28 is across the occlusion.

While the foregoing detailed description has described several embodiments of the method in accordance with this invention, it is to be understood that the above description is illustrative only and not limiting. Particularly, the invention need not be limited to a ferrule having a frusto-conical shape. It will be appreciated that a spherical ferrule could also be used within the spirit and scope of this invention. It will also be appreciated that the various elements which make up the blunt end member may be made from stainless steel, or some engineering plastic, including a suitable polymer. Additionally, while the invention has been described with regard to bypass type of operation, it will be appreciated that other medical procedures wherein a occlusion blocks an blood vessel, or substantially blocks a blood vessel, or at least prevents a guide wire from crossing the occlusion, are suitable for use with the invention described herein.

What is claimed is:

1. A method for bypassing a vascular occlusion, comprising:

positioning a distal end of an intravascular catherer adjacent to the vascular occlusion, wherein the intravascular catherer includes at least one distally mounted hinged jaw section configured for placement within a blood vessel that is movable between an open position and a closed position, and an actuation member formed with a ferrule and a guide wire tube to move at least one hinged jaw section located at the distal end of the intravascular catherer towards the open position to displace a vascular occlusion; and actuating member to move the at least one jaw section to an open position to displace the vascular occlusion.

2. The method of claim 1, further comprising:

positioning a guidewire adjacent the occlusion;

advancing the intravascular catherer along the guidewire; and positioning the intravascular catherer adjacent the vascular occlusion.

3. The method of claim 2, wherein the intravascular catherer is formed with a guidewire guide for slidable movement of the guidewire.

4. The method of claim 1 further comprising stabilizing the at least one jaw section before actuating the at least one jaw section.

5. The method of claim 4, wherein the intravascular catherer includes a balloon to stabilize the catherer at a selected location within a blood vessel.

6. The method of claim 1, wherein the at least one jaw section is fabricated from a biocompatible alloy.

7. The method of claim 1, wherein the at least one jaw section is fabricated from a nickel and titanium alloy.

8. The method of claim 1, wherein the at least one jaw section is formed with a spade-shape.

9. The method of claim 1, wherein the at least one jaw section includes a distal end having a rectangular shape.

10. The method of claim 1, wherein the at least one jaw section has a rectangular paw disposed at the distal end thereof.

11. The method of claim 1, wherein the guide wire tube is disposed in the catherer and includes a proximal end manipulable from the proximal end of the catherer and a distal end coupled to the at least one jaw section, and wherein the ferrule is coupled to the distal end of the guide wire tube and is in slidable contact with the at least one jaw section.

12. The method of claim 11, wherein the ferrule has a frusto-conical profile.

13. The method of claim 11, wherein the ferrule has a ball-shaped profile.

14. The method of claim 1, further comprising:

providing a guide wire tube disposed in the catherer, wherein the ferrule is coupled to the distal end of the guide wire tube; and manipulating a proximal end of the guide wire tube to actuate the actuating member.

15. A method for fracturing a vascular occlusion comprising:

positioning an intravascular catherer adjacent to the vascular occlusion, wherein the intravascular catherer includes an actuation member and at least one hinged end member that is configured for placement within a blood vessel, wherein the actuation member comprises a ferrule and a guide wire tube to move the at least one end member located at the distal end of the intravascular catherer towards a relatively open position to fracture the vascular occlusion;

activating the actuating member to move the at least one end member towards an open position; and displacing the vascular occlusion.

16. The method of claim 15, further comprising advancing a guidewire through a guidewire lumen of the intravascular catherer into at least a portion of the vascular occlusion.

17. The method of claim 15, wherein the intravascular catherer includes a balloon, wherein the balloon is inflated to stabilize the intravascular catherer before activating the actuating member.

18. The method of claim 15, wherein the at least one end member is fabricated from a nickel titanium alloy.

19. The method of claim 15, wherein at least one end member is spade-shaped.

20. The method of claim 15, wherein the at least one end member includes a distal end having a rectangular shape.

21. A method for fracturing an occlusion within a blood vessel, comprising:

providing an intravascular catherer comprising at least one jaw section located at the distal end of the intravascular catherer having a first position for allowing the at least one jaw section to be positioned substantially adjacent the occlusion and a second position for fracturing te occlusion;

coupling an actuation tube assembly to the at least one jaw section, wherein the actuation tube assembly includes a ferrule for moving the at least one jaw section between the first and second positions;

positioning the at least one jaw section adjacent to the occlusion while the at least one jaw section is maintained in the first position; and actuating the at least one jaw section by manipulating the actuation tube assembly; and fracturing the occlusion.

22. The method of claim 21, further comprising:

providing a guidewire lumen within the actuation tube; and advancing a guidewire through the guidewire luen towards the occlusion.

23. The method of claim 21, wherein the intravascular catherer includes a selectively activatable securing member for securing the catherer at a relatively fixed location.

24. A method for bypassing a vascular occlusion, comprising:

positioning an intravascular catherer adjacent to the vascular occlusion, wherein the intravascular cathere includes at least one hinged section coupled to an actuation member located at the distal end of the intravascular catherer, wherein the at least one hinged section is rotatably coupled among at least one open position and at least one closed position, wherein the actuation member includes a ferrule and a guide wire tube coupled to control movement of the at least one hinged section;

opening the at least one hinged section to the at least one open position in response to a force applied to the actuation member; and displacing the vascular occlusion.

\* \* \* \* \*